(12) United States Patent
Hu et al.

(10) Patent No.: US 10,987,443 B1
(45) Date of Patent: Apr. 27, 2021

(54) CONTAINER STERILIZATION DEVICE AND SYSTEM, ASSEMBLING METHOD THEREOF, AND USE THEREOF

(71) Applicants: Chio Kang Medical, Inc., Palo Alto, CA (US); Qiaokang Biotech (Guangdong) Co., LTD., Guangzhou (CN)

(72) Inventors: Shengwei Hu, Guangzhou (CN); Dongxin Hou, Guangzhou (CN); Jianlong Xue, Guangzhou (CN); Xuzhong Liao, Guangzhou (CN); Xiuling Zhong, Guangzhou (CN); Xin Yin, Guangzhou (CN); Yecheng He, Guangzhou (CN); Yuhua Zou, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/004,971

(22) Filed: Aug. 27, 2020

Related U.S. Application Data

(63) Continuation of application No. PCT/CN2020/100113, filed on Jul. 3, 2020.

(51) Int. Cl.
*A61L 9/00* (2006.01)
*A61L 2/20* (2006.01)
(Continued)

(52) U.S. Cl.
CPC .................. *A61L 2/20* (2013.01); *A61L 2/07* (2013.01); *A61L 2/24* (2013.01);
(Continued)

(58) Field of Classification Search
CPC ........ A61L 2/0082; A61L 9/00; A61L 2/0094; A61L 9/015; A61L 2/07; A61L 9/03;
(Continued)

(56) References Cited

U.S. PATENT DOCUMENTS

| 1,954,056 A | 4/1934 | Miller |
| 2,817,689 A | 12/1957 | White |

(Continued)

FOREIGN PATENT DOCUMENTS

| CN | 1223166 A | 7/1999 |
| CN | 101224381 A | 7/2008 |

(Continued)

OTHER PUBLICATIONS

International Application No. PCT/CN2020/101140 as prepared by the Chinese International Searching Authority filed on Jul. 9, 2020, 59 pages.
(Continued)

*Primary Examiner* — Monzer R Chorbaji
(74) *Attorney, Agent, or Firm* — Adsero IP (57) ABSTRACT

The present disclosure discloses a container sterilization device and system, an assembling method and use thereof. The container sterilization device includes a sterilization gas supply assembly, a gas circulation assembly, and a heating and humidification assembly. The sterilization gas supply assembly includes a chemical feeding pipeline. The gas circulation assembly includes a gas circulation pipeline, a gas extraction pipeline, and a vacuum pump disposed on the gas extraction pipeline. The heating and humidification assembly includes a thermostatic water tank, a steam generator, a first connecting pipeline, and a humidity feeding pipeline. The first connecting pipeline is configured to provide fluid communication between the thermostatic water tank and the steam generator, while the humidity
(Continued)

feeding pipeline is configured to be in fluid communication with the steam generator. The chemical feeding pipeline, the gas circulation pipeline, and the gas extraction pipeline are each at least partially located in the thermostatic water tank.

20 Claims, 4 Drawing Sheets

(51) Int. Cl.
    *A61L 2/07*     (2006.01)
    *A61L 2/24*     (2006.01)

(52) U.S. Cl.
    CPC ... *A61L 2202/121* (2013.01); *A61L 2202/123* (2013.01); *A61L 2202/14* (2013.01); *A61L 2202/15* (2013.01); *A61L 2202/16* (2013.01); *A61L 2202/23* (2013.01)

(58) Field of Classification Search
    CPC .......... A61L 2/20; A61L 2209/00; A61L 2/26; A61L 2209/21
    USPC .................................................. 422/305–306
    See application file for complete search history.

(56) References Cited

U.S. PATENT DOCUMENTS

| | | | |
|---|---|---|---|
| 3,022,054 A | 2/1962 | Kotzebue | |
| 3,844,739 A | 10/1974 | Alfrey, Jr. | |
| 3,961,920 A | 6/1976 | Gilbert | |
| 3,997,633 A | 12/1976 | Leva et al. | |
| 4,112,054 A | 9/1978 | Feingold et al. | |
| 4,119,539 A | 10/1978 | Ettel et al. | |
| 4,243,636 A | 1/1981 | Shiraki et al. | |
| 4,301,113 A | 11/1981 | Alguire et al. | |
| 4,517,167 A | 5/1985 | Popescu et al. | |
| 4,831,196 A | 5/1989 | Buonicore et al. | |
| 5,084,075 A | 1/1992 | Sircar | |
| 5,204,075 A | 4/1993 | Jain et al. | |
| 5,283,035 A | 2/1994 | Karthaus et al. | |
| 5,290,345 A | 3/1994 | Osendorf et al. | |
| 5,511,409 A | 4/1996 | Knaebel | |
| 5,741,470 A | 4/1998 | Wenzler | |
| 5,755,857 A | 5/1998 | Acharya et al. | |
| 5,779,773 A | 7/1998 | Cam et al. | |
| 5,964,927 A | 10/1999 | Graham et al. | |
| 6,156,101 A | 12/2000 | Naheiri | |
| 6,684,648 B2 | 2/2004 | Faqih | |
| 6,743,402 B2 | 6/2004 | Shimakawa | |
| 2002/0046569 A1 | 4/2002 | Faqih | |
| 2002/0197194 A1 | 12/2002 | Machado et al. | |
| 2006/0236860 A1 | 10/2006 | Sumida et al. | |
| 2006/0249027 A1 | 11/2006 | Adolphsen et al. | |
| 2007/0209383 A1 | 9/2007 | Hutton | |
| 2008/0078289 A1 | 4/2008 | Sergi et al. | |
| 2008/0080999 A1 | 4/2008 | Bondar | |
| 2010/0196194 A1 | 8/2010 | Voeten et al. | |
| 2011/0265644 A1 | 11/2011 | Swami et al. | |
| 2012/0031268 A1 | 2/2012 | Yaghi et al. | |
| 2014/0119989 A1* | 5/2014 | Hayashi ................. | C01B 21/36 422/28 |
| 2014/0290162 A1* | 10/2014 | Tanimoto ................. | B25J 21/02 52/234 |
| 2016/0010883 A1* | 1/2016 | Jornitz ................... | E04H 1/005 454/187 |
| 2017/0056813 A1 | 3/2017 | McMahon et al. | |
| 2019/0076776 A1 | 3/2019 | Mahecha-Botero et al. | |
| 2019/0151791 A1 | 5/2019 | Awadh et al. | |

FOREIGN PATENT DOCUMENTS

| | | |
|---|---|---|
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102921570 A | 2/2013 |
| CN | 202802975 U | 3/2013 |
| CN | 202933710 U | 5/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 106475021 A | 3/2017 |
| CN | 106582126 A | 4/2017 |
| CN | 206535551 U | 10/2017 |
| CN | 206853397 U | 1/2018 |
| CN | 107677016 A | 2/2018 |
| CN | 207169397 U | 4/2018 |
| CN | 207187436 U | 4/2018 |
| CN | 207745676 U | 8/2018 |
| CN | 207913454 U | 9/2018 |
| CN | 108607511 A | 10/2018 |
| CN | 208218734 U | 12/2018 |
| CN | 109382064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| WO | WO2011002277 A1 | 1/2011 |
| WO | WO2019236249 A1 | 12/2019 |

OTHER PUBLICATIONS

U.S. Appl. No. 17/012,857, TrackOne Bypass CON Application filed on Sep. 4, 2020, 148 pages.
International Application No. PCT/CN2020/100143 as prepared by the Chinese International Searching Authority filed on Jul. 3, 2020, 25 pages.
U.S. Appl. No. 17/002,500, TrackOne Bypass CON Application filed on Aug. 25, 2020, 61 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed on Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
U.S. Appl. No. 17/002,529, TrackOne Bypass CON Application filed on Aug. 25, 2020, 64 pages.
International Application No. PCT/CN2020/100119 as prepared by the Chinese International Searching Authority filed on Jul. 3, 2020, 29 pages.

(56) References Cited

OTHER PUBLICATIONS

U.S. Appl. No. 17/002,540, TrackOne Bypass CON Application filed on Aug. 25, 2020, 89 pages.
International Application No. PCT/CN2020/100120 as prepared by the Chinese International Searching Authority filed on Jul. 3, 2020, 28 pages.
U.S. Appl. No. 17/004,730, TrackOne Bypass CON Application filed on Aug. 27, 2020, 77 pages.
International Application No. PCT/CN2020/101142 as prepared by the Chinese International Searching Authority filed on Jul. 9, 2020, 29 pages.
U.S. Appl. No. 17/012,864, TrackOne Bypass CON Application filed on Sep. 4, 2020, 78 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed on Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
U.S. Appl. No. 17/004,930, TrackOne Bypass CON Application filed on Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed on Jul. 3, 2020, 35 pages.
U.S. Appl. No. 17/012,857, Non-Final Office Action, dated Nov. 24, 2020, 13 pages.
U.S. Appl. No. 17/002,540, Office Action-Restriction Requirement, dated Dec. 1, 2020, 7 pages.
U.S. Appl. No. 17/002,500, Non-Final Office Action dated Dec. 8, 2020, 109 pages.
Kahm et al., 2018 "Lyapunov exponents with Model Predictive Control for exothermic batch reactors" IFAC-PapersOnline, 51, 417-422.
U.S. Appl. No. 17/002,523 Notice of Allowance, dated Dec. 17, 2020, 35 pages.
U.S. Appl. No. 17/004,930 Office Action-Restriction Requirement, dated Dec. 18, 2020, 8 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/002,529, Non-Final Office Action-Restriction Requirement dated Feb. 17, 2021, 11 pages.

\* cited by examiner

CONTAINER STERILIZATION DEVICE AND SYSTEM, ASSEMBLING METHOD THEREOF, AND USE THEREOF

CROSS-REFERENCE TO RELATED PATENT APPLICATIONS

This application is a continuation of International Application No. PCT/CN2020/100113, filed on Jul. 3, 2020, which is incorporated herein by reference in its entirety for all purposes.

TECHNICAL FIELD

The present disclosure relates to the field of sterilization technology, and more particularly, to a container sterilization device and system, an assembling method thereof, and a use thereof.

BACKGROUND

As a carrying tool, a shipping container (herein referred to simply as "container" or the like) travels around the world along with other transportation vehicles such as ships, trucks, automobiles, and the like, loads different goods during transportation, and goes through different regions and environments. As a result, the container can carry various microorganisms including various pathogenic microorganisms, which are likely to cause contamination when staying at a port or during loading and unloading, thereby causing occurrence and prevalence of related diseases. Especially during an epidemic, such contamination is more likely to lead to widespread dissemination of the epidemic across regions. In this regard, in accordance with requirements of the International Health Regulations, the port is required to preventively disinfect containers and loaded goods entering and leaving the port.

At present, the methods for sterilizing the containers mainly include a fumigation disinfection method and a spray disinfection method. That is, chemical disinfectants are used to disinfect the containers and goods loaded by the containers by fumigation and spraying. Commonly used disinfectants include calcium hypochlorite, sodium hypochlorite, chlorine dioxide, peroxyacetic acid, hydrogen peroxide, glutaraldehyde, formaldehyde, low-concentration ethylene oxide, iodophor, and the like. The disinfection effects of the chemical disinfectants are limited and influenced by various factors, such as the type of good and the type, concentration, action time, and environment of the disinfectants, and the like. If the chemical disinfectants are not treated properly, the disinfection effects cannot meet the requirements or affect disinfection objects. In addition, there are various types of disinfectants, and the preparation and use of the disinfectants have significant differences depending on the type of the disinfectants. The application and the operational processes are also different, the influence factors are greater, and the evaluation of the disinfection effect is inconvenient. Moreover, at present, the fumigation disinfection method and the spray disinfection method are mostly carried out by manual operations, resulting in the operation being inconvenient, the effect being poor, and there being potential safety hazards.

Hence, there is a need for more robust and scalable solutions for implementing sterilization technologies, and, more particularly, for implementing a container sterilization device and system, an assembling method thereof, and a use thereof.

SUMMARY

The present disclosure provides a container sterilization device and system, an assembling method and a use thereof, which are convenient to operate, good in terms of sterilization effect, safe, and reliable.

In one aspect of the present disclosure, a container sterilization device may be provided, including a sterilization gas supply assembly, a gas circulation assembly, and a heating and humidification assembly. The sterilization gas supply assembly includes a chemical feeding pipeline provided with a chemical feeding opening. The gas circulation assembly includes a vacuum pump, a gas circulation pipeline provided with a gas charging opening, and a gas extraction pipeline provided with a gas extraction opening. The heating and humidification assembly includes a thermostatic water tank, a steam generator, a first connecting pipeline, and a humidity feeding pipeline provided with a humidity feeding opening. The chemical feeding pipeline may be at least partially located in the thermostatic water tank. An end of the gas circulation pipeline that is opposite from the gas charging opening may be configured to be in fluid communication with an end of the gas extraction pipeline that is opposite from the gas extraction opening. A joint connecting the gas circulation pipeline with the gas extraction pipeline and a portion of pipelines adjacent to the joint may be located in the thermostatic water tank. The vacuum pump may be disposed on the gas extraction pipeline, between the gas extraction opening and the thermostatic water tank. The first connecting pipeline may be configured to provide fluid communication between the thermostatic water tank and the steam generator. An end of the humidity feeding pipeline that is opposite from the humidity feeding opening may be configured to be in fluid communication with the steam generator.

In the container sterilization device, the chemical feeding pipeline of the sterilization gas supply assembly can supply sterilization gas into a container through the chemical feeding opening. In the heating and humidification assembly, the steam generator can vaporize water in the thermostatic water tank into steam, which may be supplied to the container through the humidity feeding opening of the humidity feeding pipeline, thereby providing a suitable sterilization humidity environment in the container. In addition, the thermostatic water tank can also heat the chemical feeding pipeline to further heat and vaporize the sterilization substance in the chemical feeding pipeline, thereby producing more sterilization gas. Moreover, the gas circulation assembly can extract the gas in the container through the gas extraction pipeline using the vacuum pump, and the gas may be further heated in the thermostatic water tank and may return to the container through the gas circulation pipeline. Such circulation may be repeated to improve the sterilization effect. The aforementioned container sterilization device is convenient to operate, good in terms of sterilization effect, safe, and reliable.

In another aspect of the present disclosure, a container sterilization system may be further provided in one of the embodiments, including a container and the aforementioned container sterilization device. The chemical feeding opening, the gas charging opening, the gas extraction opening, and the humidity feeding opening may be in fluid communication with an interior of the container.

In yet another aspect of the present disclosure, a method for assembling a container sterilization device may be further provided, which includes (in the order as follows or in no particular order): providing a sterilization gas supply assembly, the sterilization gas supply assembly including a chemical feeding pipeline provided with a chemical feeding opening; providing a gas circulation assembly including a vacuum pump, a gas circulation pipeline provided with a gas charging opening and a gas extraction pipeline provided with a gas extraction opening; and providing a heating and humidification assembly including a thermostatic water tank, a steam generator, a first connecting pipeline, and a humidity feeding pipeline provided with a humidity feeding opening. The method might further comprise (in the order as follows or in no particular order): fluidly coupling the thermostatic water tank with the steam generator using the first connecting pipeline; fluidly coupling an end of the humidity feeding pipeline that is opposite from the humidity feeding opening with the steam generator; inserting at least a portion of the chemical feeding pipeline in the thermostatic water tank; fluidly coupling an end of the gas circulation pipeline that is opposite from the gas charging opening with an end of the gas extraction pipeline that is opposite from the gas extraction opening; inserting a joint connecting the gas circulation pipeline with the gas extraction pipeline and a portion of pipelines adjacent to the joint in the thermostatic water tank; and positioning the vacuum pump on the gas extraction pipeline, between the gas extraction opening and the thermostatic water tank.

In yet another aspect of the present disclosure, a method for assembling a container sterilization system may be further provided, including providing the aforementioned container sterilization device or the container sterilization device assembled according to the aforementioned method; providing a container; and providing fluid communication between an interior of the container and each of the chemical feeding opening, the gas charging opening, the gas extraction opening, and the humidity feeding opening.

In yet another aspect of the present disclosure, a method for sterilizing a container may be further provided, which includes: sterilizing a container using the aforementioned container sterilization device or the container sterilization system, using the following steps: S1, injecting water into the thermostatic water tank through the humidity feeding pipeline; S2, heating the thermostatic water tank to a first preset temperature to supply water to the steam generator and to supply heat to each of the gas circulation pipeline and the chemical feeding pipeline; S3, switching on the vacuum pump to vacuumize the container until an air pressure in the container reaches a first preset air pressure; S4, directing the water in the thermostatic water tank to enter the container through the steam generator via the humidity feeding pipeline to humidify the container; and S5, injecting the sterilization gas into the container after the sterilization gas is heated and vaporized by the heated chemical feeding pipeline until the air pressure in the container reaches a second preset air pressure.

In still another aspect of the present disclosure, use of the aforementioned container sterilization device or the aforementioned container sterilization device assembled according to the aforementioned method in container sterilization may be further provided.

The container sterilization system includes the aforementioned container sterilization device and thus has the technical effects of the aforementioned container sterilization device, that is, the operation is convenient, the sterilization effect is good, and it is safe and reliable.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DESCRIPTION OF REFERENCE NUMERALS

10—container sterilization device; 110—chemical feeding pipeline; 130—first temperature sensor; 140—first check valve; 151—first valve; 210—vacuum pump; 220—gas circulation pipeline; 230—gas extraction pipeline; 240—pressure sensor; 251—first temperature and humidity sensor; 252—second temperature and humidity sensor; 261—third valve; 262—thirteenth valve; 270—ventilation branch pipeline; 280—air filter; 310—thermostatic water tank; 311—second temperature sensor; 312—liquidometer; 320—steam generator; 330—first connecting pipeline; 340—humidity feeding pipeline; 351—fourth valve; 352—fifth valve; 353—fourteenth valve; 410—exhaust pipeline; 420—second connecting pipeline; 430—third connecting pipeline; 440—fourth connecting pipeline; 450—fan; 460—sterilization waste gas treater; 471—tenth valve; 472—eleventh valve; 481—second check valve; 482—third check valve; 491—sterilization substrate storage tank; 492—waste liquid recovery tank; 493—waste liquid recovery pipeline; 494—sterilization substrate liquid feeding pipeline; 495—circulation pump; 496a—sixth valve; 496b—seventh valve; 496c—eighth valve; 496d—ninth valve; 496e—fifteenth valve; 510—water feeding pipeline; 511—water feeding opening; 520—first water inlet pipeline; 530—first water outlet pipeline; 540—water filter; 551—twelfth valve; 552—sixteenth valve; 560—second water inlet pipeline; 570—second water outlet pipeline; 580—discharge pipeline; 600—mobile vehicle-mounted assembly; 700—parking support assembly; 810—pipeline fixing rack; 820—pipeline fixing support arm; 830—fixing rack support; 910—controller; 920—power supply; 930—control interface; 20—container.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In one aspect of the present disclosure, a container sterilization device 10 is provided, which can include, but is not limited to, a sterilization gas supply assembly, a gas circulation assembly, and a heating and humidification assembly. The sterilization gas supply assembly may include a chemical feeding pipeline 110 provided with a chemical feeding opening. The gas circulation assembly may include a vacuum pump 210, a gas circulation pipeline 220 provided with a gas charging opening, and a gas extraction pipeline 230 provided with a gas extraction opening. The heating and humidification assembly may include a thermostatic water tank 310, a steam generator 320, a first connecting pipeline 330, and a humidity feeding pipeline 340 provided with a humidity feeding opening. The first connecting pipe 330 may be configured to provide fluid communication between the thermostatic water tank 310 and the steam generator 320. An end of the humidity feeding pipeline 340 that is opposite from the humidity feeding opening may be configured to be in fluid communication with the steam generator 320. The chemical feeding pipeline 110 may be at least partially located in the thermostatic water tank 310. An end of the gas circulation pipeline 220 that is opposite from the gas charging opening may be configured to be in fluid communication with an end of the gas extraction pipeline 230 that is opposite from the gas extraction opening. A joint connecting the gas circulation pipeline 220 with the gas extraction pipeline 230 and a portion of pipelines adjacent to the joint may be located in the thermostatic water tank 310. The vacuum pump 210 may be disposed on the gas extraction pipeline 230, between the gas extraction opening and the thermostatic water tank 310.

In some of the embodiments, at least one of the chemical feeding pipeline 110, the gas circulation pipeline 220, or the gas extraction pipeline 230, and/or the like, of the aforementioned container sterilization device 10 may be at least partially disposed in the thermostatic water tank 310 in a spirally folded manner.

In some of the embodiments, the sterilization gas supply assembly of the aforementioned container sterilization device 10 may further include, without limitation, a first gas filter (not shown), a first temperature sensor 130, a first check valve 140, a first valve 151, and a second valve (not shown). The first gas filter, the first temperature sensor 130, the first check valve 140, the first valve 151, and the second valve may each be disposed on the chemical feeding pipeline 110. The first gas filter and the first temperature sensor 130 may each be located between the thermostatic water tank 310 and the chemical feeding opening. The first check valve 140 may be located between the thermostatic water tank 310 and the first temperature sensor 130. The first valve 151 may be located at a side of the first check valve 140, adjacent to the first temperature sensor 130.

In some of the embodiments, the sterilization gas supply assembly of the aforementioned container sterilization device 10 may further include, but is not limited to, a pressure sensor 240, a first temperature and humidity sensor 251, a second temperature and humidity sensor 252, and a third valve 261. The pressure sensor 240 may be disposed on the gas circulation pipeline 220 and located between the gas charging opening and the thermostatic water tank 310. The first temperature and humidity sensor 251, the second temperature and humidity sensor 252, and the third valve 261 may each be disposed on the gas extraction pipeline 230. The first temperature and humidity sensor 251 and the second temperature and humidity sensor 252 may be located between the vacuum pump 210 and the gas charging opening, spaced apart from each other. The third valve 261 may be located between the vacuum pump 210 and the thermostatic water tank 310.

In some of the embodiments, the heating and humidification assembly of the aforementioned container sterilization device 10 may further include, without limitation, a fourth valve 351 and a fifth valve 352. The fourth valve 351 may be disposed on the humidity feeding pipeline 340 and may be located between the steam generator 320 and the humidity feeding opening. The fifth valve 352 may be disposed between the thermostatic water tank 310 and the steam generator 320.

In some of the embodiments, the aforementioned container sterilization device 10 may further include a sterilization waste gas treatment assembly. The sterilization waste gas treatment assembly may include, but is not limited to, an exhaust pipeline 410, a second connecting pipeline 420, a third connecting pipeline 430, a fourth connecting pipeline 440, a fan 450, a sterilization waste gas treater 460, and a sterilization substrate circulation changer. The second connecting pipeline 420 may be configured to provide fluid communication between the fan 450 and the vacuum pump 210. The third connecting pipeline 430 may be configured to provide fluid communication between the fan 450 and the sterilization waste gas treater 460. The fourth connecting pipeline 440 may be configured to provide fluid communication between the sterilization waste gas treater 460 and the sterilization substrate circulation changer. The exhaust pipeline 410 may be configured to provide fluid communication between the sterilization waste gas treater 460 and the outside environment (i.e., the environment external to the container sterilization device 10, or the like).

In some of the embodiments, the aforementioned sterilization substrate circulation changer may further include, without limitation, a sterilization substrate storage tank 491, a waste liquid recovery tank 492, a waste liquid recovery pipeline 493, and a sterilization substrate liquid feeding pipeline 494. The waste liquid recovery pipeline 493 may be configured to provide fluid communication between the waste liquid recovery tank 492 and the fourth connecting pipeline 440, and the sterilization substrate liquid feeding pipeline 494 may be configured to provide fluid communication between the sterilization substrate storage tank 491 and the fourth connecting pipeline 440.

In some of the embodiments, the aforementioned sterilization substrate circulation changer may further include, but is not limited to, a circulation pump 495 disposed on the waste liquid recovery pipeline 493.

In some of the embodiments, the aforementioned sterilization substrate circulation changer may further include, without limitation, a sixth valve 496a, a seventh valve 496b, an eighth valve 496c, and a ninth valve 496d. The sixth valve 496a may be disposed on the waste liquid recovery pipeline 493 and may be located between the waste liquid recovery tank 492 and the circulation pump 495. The seventh valve 496b may be located at a junction of the waste liquid recovery pipeline 493, the sterilization substrate liquid feeding pipeline 494, and the fourth connecting pipeline 440. The eighth valve 496c may be located on the fourth connecting pipeline 440. The ninth valve 496d may be located on the sterilization substrate liquid feeding pipeline 494.

In some of the embodiments, the sterilization waste gas treatment assembly of the aforementioned container sterilization device 10 may further include, but is not limited to, a tenth valve 471, an eleventh valve 472, a second check valve 481, and a third check valve 482. The tenth valve 471 may disposed on the second connecting pipeline 420, while the eleventh valve 472 may disposed on the third connecting pipeline 430. The second check valve 481 may disposed on the third connecting pipeline 430, while the third check valve 482 may disposed on the exhaust pipeline 410.

In some of these embodiments, the aforementioned container sterilization device 10 may further include, without limitation, a cooling assembly, which may include a water feeding pipeline 510, a first water inlet pipeline 520, and a first water outlet pipeline 530. The water feeding pipeline 510 may be provided with a water feeding opening 511 configured to be in fluid communication with a water source. In addition, the sterilization waste gas treater 460 of the container sterilization device 10 may further have a first cooling water interlayer, and the first cooling water interlayer may be provided with a first cooling water interlayer inlet and a first cooling water interlayer outlet. The first water inlet pipeline 520 may be configured to provide fluid communication between the first cooling water interlayer inlet and the water feeding pipeline 510, and the first water outlet pipeline 530 may be configured to be in fluid communication with the first cooling water interlayer outlet to discharge cooling water from the first cooling water interlayer.

In some of the embodiments, the aforementioned cooling assembly may further include, but is not limited to, a water filter 540 and a twelfth valve 551. The water filter 540 may be disposed on the water feeding pipeline 510 and may be located between the water feeding opening 511 and a joint of the first water inlet pipeline 520 and the water feeding pipeline 510. The twelfth valve 551 may be disposed on the first water inlet pipeline 520.

In some of the embodiments, the aforementioned cooling assembly may further include, without limitation, a second water inlet pipeline 560 and a second water outlet pipeline 570. In addition, the vacuum pump 210 of the gas circulation assembly may have a second cooling water interlayer, which may be provided with a second cooling water interlayer inlet and a second cooling water interlayer outlet. The second water inlet pipeline 560 may be configured to provide fluid communication between the second cooling water interlayer inlet and the water feeding pipeline 510, and the second water outlet pipeline 570 may be configured to be in fluid communication with the second cooling water interlayer outlet to discharge the cooling water from the second cooling water interlayer.

In some of the embodiments, the aforementioned cooling assembly may further include a sixteenth valve 552 disposed on the second water inlet pipeline 560.

In some of the embodiments, the aforementioned container sterilization device 10 may further include, but is not limited to, a mobile vehicle-mounted assembly 600. The sterilization gas supply assembly, the gas circulation assembly, and the heating and humidification assembly can each be mounted on the mobile vehicle-mounted assembly 600. The mobile vehicle-mounted assembly 600 can be configured to connect to the container 20.

In some of these embodiments, the mobile vehicle-mounted assembly 600 may be a truck transportation assembly. Alternatively, in some of the embodiments, the mobile vehicle-mounted assembly 600 may include, without limitation, a mobile carriage and a semi-trailer tractor, and the mobile carriage may be fixed on the semi-trailer tractor.

Figure 3:
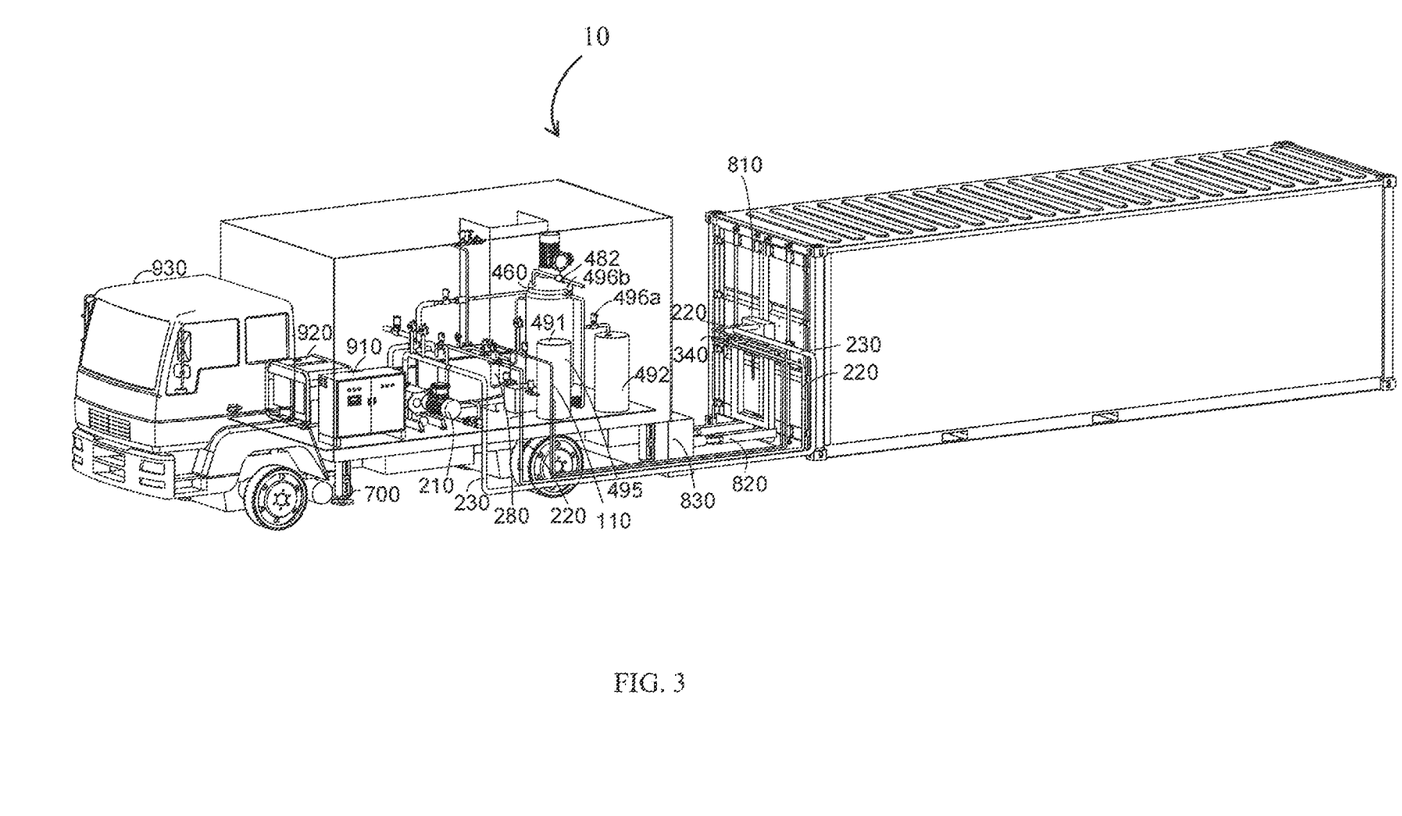
FIG. 3 is a perspective view of the container sterilization system according to one of the embodiments of the present disclosure as shown in FIG. 1 from another perspective.

In some of the embodiments, the aforementioned container sterilization device 10 may further include, but is not limited to, a parking support assembly 700 (as shown in FIG. 3), which may be mounted below the mobile vehicle-mounted assembly 600 and may be used to support the mobile vehicle-mounted assembly 600.

In some of the embodiments, the aforementioned container sterilization device 10 may further include a pipeline fixing support assembly which may include, without limitation, a pipeline fixing rack 810, a pipeline fixing support arm 820, and a fixing rack support 830. The gas circulation pipeline 220, the gas extraction pipeline 230, the chemical feeding pipeline 110, and the humidity feeding pipeline 340 of the container sterilization device 10 may each be fixed on the pipeline fixing rack 810. An end of the gas circulation pipeline 220 provided with the gas charging opening, an end of the gas extraction pipeline 230 provided with the gas extraction opening, an end of the chemical feeding pipeline 110 provided with the chemical feeding opening, and an end of the humidity feeding pipeline 340 provided with the humidity feeding opening can pass through the pipeline fixing rack 810. The fixing rack support 830 may be fixed on one side of the mobile vehicle-mounted assembly 600. Each of the two ends of the pipeline fixing support arm 820 may respectively be fixed on one or the other of the pipeline fixing rack 810 and the fixing rack support 830. The fixing rack support 830 may be configured to control the pipeline fixing support arm 820 to move the pipeline fixing rack 810.

In some of the embodiments, the aforementioned container sterilization device 10 may further include, but is not limited to, a controller 910, and the vacuum pump 210, the thermostatic water tank 310, and the steam generator 320 may each be electrically coupled to the controller 910. The controller 910 may be configured to control corresponding operations of each of the vacuum pump 210, the thermostatic water tank 310, and the steam generator 320.

In yet another aspect of the present disclosure, a container sterilization system may be further provided, which may include, without limitation, a container 20 and the container sterilization device 10 of any one of the aforementioned embodiments of the present disclosure. The chemical feeding opening, the gas charging opening, the gas extraction opening, and the humidity feeding opening of the container sterilization device 10 may each be in fluid communication with the inside or interior of the container 20.

In yet another aspect of the present disclosure, a method for assembling a container sterilization device 10 may be further provided, which may include providing a sterilization gas supply assembly including a chemical feeding pipeline 110 provided with a chemical feeding opening; providing a gas circulation assembly including a vacuum pump 210, a gas circulation pipeline 220 provided with a gas charging opening, and a gas extraction pipeline 230 provided with a gas extraction opening; and providing a heating and humidification assembly including a thermostatic water tank 310, a steam generator 320, a first connecting pipeline 330, and a humidity feeding pipeline 340 provided with a humidity feeding opening. The method might further include fluidly coupling the thermostatic water tank 310 with the steam generator 320 using the first connecting pipeline 330; fluidly coupling an end of the humidity feeding pipeline 340 that is opposite from the humidity feeding opening with the steam generator 320; inserting a portion of the chemical feeding pipeline 110 in the thermostatic water tank 310; fluidly coupling an end of the gas circulation pipeline 220 that is opposite from the gas charging opening with an end of the gas extraction pipeline 230 that is opposite from the gas extraction opening; placing a joint connecting the gas circulation pipeline 220 with the gas extraction pipeline 230 and a portion of pipelines adjacent to the joint in the thermostatic water tank 310; and positioning the vacuum pump 210 on the gas extraction pipeline 230, between the gas extraction opening and the thermostatic water tank 310. Although the steps of the method above are described as being in a particular order, the various embodiments are not so limited, and the order of the above-described steps may be changed as necessary or as desired. In other words, the steps of the method above may be performed in any order, as appropriate or as desired.

In yet another aspect of the present disclosure, a method for assembling a container sterilization system may be further provided, which may include providing the aforementioned container sterilization device 10 or the container sterilization device 10 assembled according to the aforementioned method; providing a container 20; and providing fluid communication between an interior of the container 20 and each of the chemical feeding opening, the gas charging opening, the gas extraction opening, and the humidity feeding opening.

In yet another aspect of the present disclosure, a method for sterilizing a container 20 may be further provided, which may include: sterilizing a container 20 using the aforementioned container sterilization device 10 or the container sterilization system of the aforementioned aspects of the present disclosure.

In some of the embodiments, the aforementioned method may include the following steps:

S1, injecting water into the thermostatic water tank 310 through the humidity feeding pipeline 340;

S2, heating the thermostatic water tank 310 to a first preset temperature to supply water to the steam generator 320 and to supply heat to each of the gas circulation pipeline 220 and the chemical feeding pipeline 110;

S3, switching on the vacuum pump 210 to vacuumize the container 20 until an air pressure in the container 20 reaches a first preset air pressure;

S4, directing the water in the thermostatic water tank 310 to enter the container 20 through the steam generator 320 via the humidity feeding pipeline 340 to humidify the container 20; and S5, injecting the sterilization gas into the container 20 after the sterilization gas is heated and vaporized by the heated chemical feeding pipeline 110 until the air pressure in the container 20 reaches a second preset air pressure.

In some of the embodiments, the first preset temperature may be within a range from 60° C. to 80° C., the first preset air pressure may be within a range from −30 kPa to −70 kPa, and the second preset air pressure may be within a range from 20 kPa to 50 kPa.

In some of the embodiments, the aforementioned method may further include: repeating steps S3 to S5 for a plurality of times for a preset time period; maintaining a temperature inside the container 20 at a second preset temperature; and maintaining a humidity inside the container 20 at a preset humidity.

In some of the embodiments, the preset time period may be within a range from 6 h to 8 h, the second preset temperature may be within a range from 40° C. to 50° C., and the preset humidity (in terms of percent relative humidity ("% RH")) may be within a range from 50% RH to 70% RH.

In still another aspect of the present disclosure, use of the container sterilization device 10 or the container sterilization system for container sterilization of the aforementioned aspects of the present disclosure is further provided.

Figure 1:
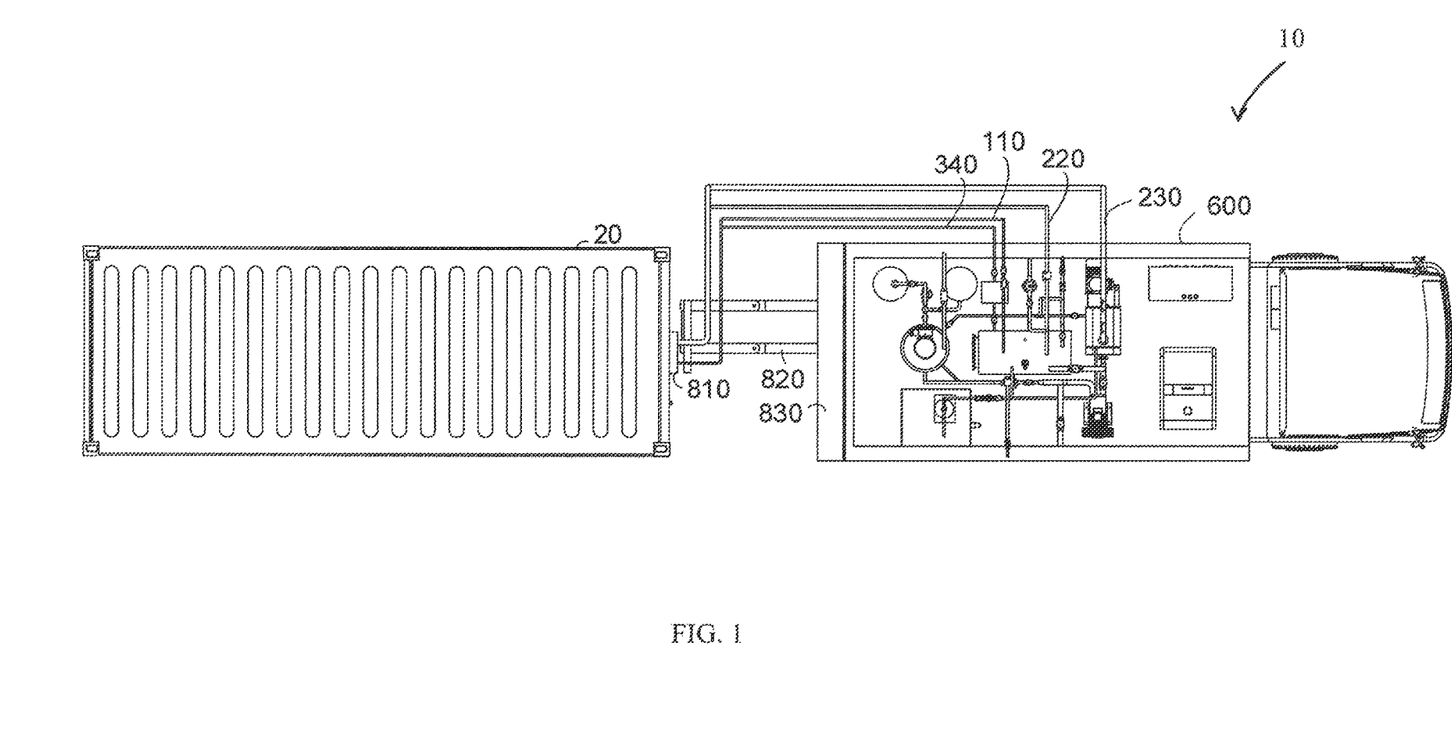
FIG. 1 is a top view of a container sterilization system according to one of the embodiments of the present disclosure.

As shown in FIG. 1, one of the embodiments of the present disclosure provides a container sterilization system, which includes a container sterilization device 10 and a container 20. The container sterilization system is convenient to operate, good in terms of sterilization effect, safe, and reliable.

Figure 2:
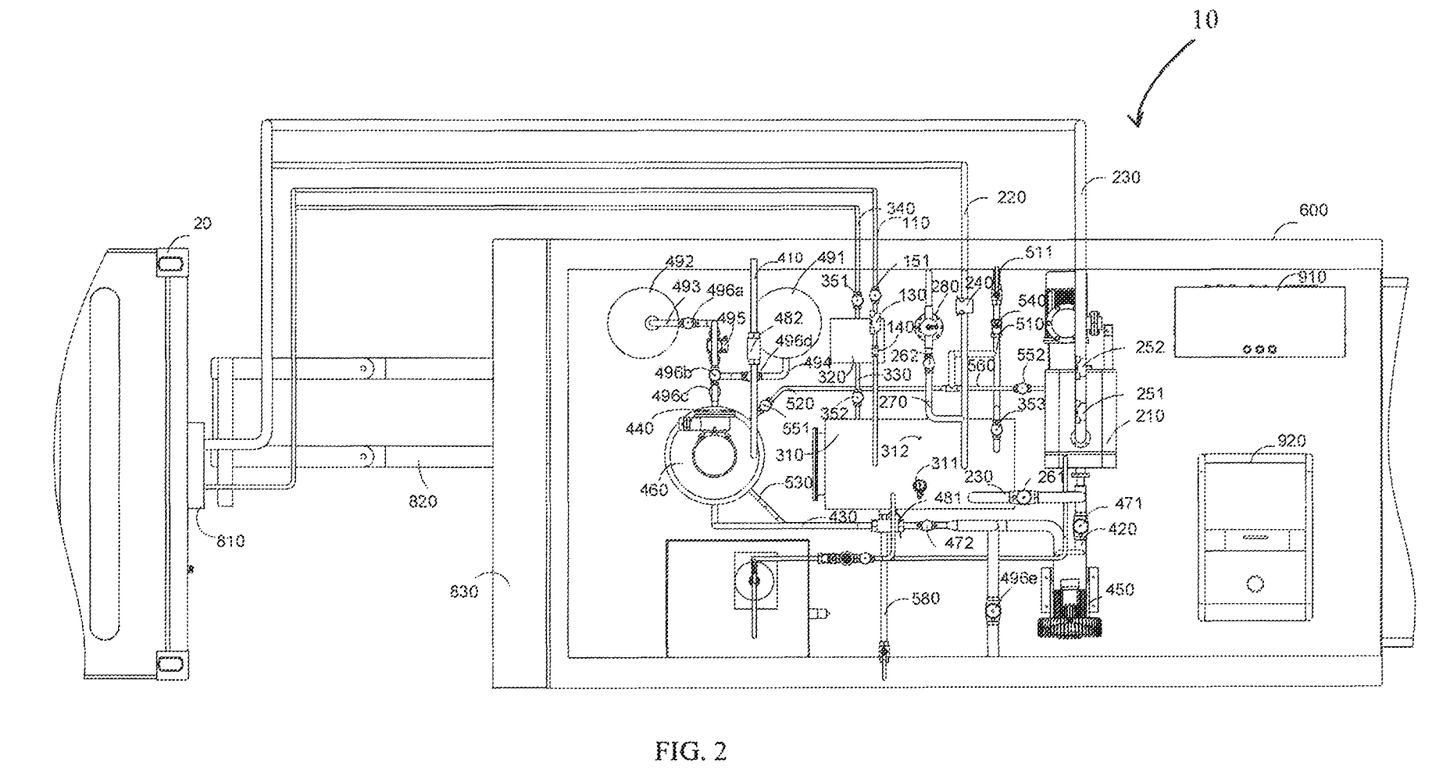
FIG. 2 is a partial enlarged view of the container sterilization system according to one of the embodiments of the present disclosure as shown in FIG. 1.

Specifically, as shown in FIGS. 1 to 3, the container sterilization device 10 includes a sterilization gas supply assembly, a gas circulation assembly, a heating and humidification assembly, a sterilization waste gas treatment assembly, a cooling assembly, a mobile vehicle-mounted assembly 600, a parking support assembly 700, a pipeline fixing support assembly, and a control assembly. The operations of the sterilization gas supply assembly, the gas circulation assembly, the heating and humidification assembly, the sterilization waste gas treatment assembly, the cooling assembly, the mobile vehicle-mounted assembly 600, the parking support assembly 700, and the pipeline fixing support assembly may be controlled by the control assembly. The sterilization gas supply assembly, the gas circulation assembly, the heating and humidification assembly, the sterilization waste gas treatment assembly, the cooling assembly, and the control assembly may be mounted on the mobile vehicle-mounted assembly 600. The sterilization gas supply assembly injects the sterilization gas into the container 20 after being heated and vaporized by the heating and humidification assembly. In addition, the heating and humidification assembly heats and humidifies the container 20. The gas circulation assembly may be used for circulation of sterilization gas, while the cooling assembly may be used to cool the gas circulation assembly and the sterilization waste gas treatment assembly, and the sterilization waste gas treatment assembly may be used for treating the sterilization waste gas.

Specifically, the sterilization gas supply assembly includes a chemical feeding pipeline 110 provided with a chemical feeding opening, which may be configured to be in fluid communication with the inside or interior of the container 20, so as to supply the sterilization gas to the inside or interior of the container 20. The gas circulation assembly includes a vacuum pump 210, a gas circulation pipeline 220 provided with a gas charging opening, and a gas extraction pipeline 230 provided with a gas extraction opening. The heating and humidification assembly includes a thermostatic water tank 310, a steam generator 320, a first connecting pipeline 330, and a humidity feeding pipeline 340. The first connecting pipeline 330 may be used to provide fluid communication between the thermostatic water tank 310 and the steam generator 320. The humidity feeding pipeline 340 may be provided with a humidity feeding opening, and an end of the humidity feeding pipeline 340 that is opposite from the humidity feeding opening may be in fluid communication with the steam generator 320. The chemical feeding pipeline 110 may be at least partially located in the thermostatic water tank 310. An end of the gas circulation pipeline 220 that is opposite from the gas charging opening may be in fluid communication with an end of the gas extraction pipeline 230 that is opposite from the gas extraction opening. A joint connecting the gas circulation pipeline 220 with the gas extraction pipeline 230 and a portion of pipelines adjacent to the joint may be located in the thermostatic water tank 310. The vacuum pump 210 may be disposed on the gas extraction pipeline 230 and may be located between the gas extraction opening and the thermostatic water tank 310.

In some embodiments, the chemical feeding pipeline 110, the gas circulation pipeline 220, and the gas extraction pipeline 230 may each be at least partially disposed in the thermostatic water tank 310 in a spirally folded manner. The thermostatic water tank heats the chemical feeding pipeline 110 arranged therein, and the chemical feeding pipeline 110 may be at least partially arranged in the thermostatic water tank in the spirally folded manner, which increases the path and time for the sterilization gas passing through the thermostatic water tank 310, to more fully and effectively heat and vaporize the sterilization gas passing through the thermostatic water tank 310. Similarly, the gas circulation pipeline 220 and the gas extraction pipeline 230 may each be at least partially arranged in the thermostatic water tank in the spirally folded manner, which can also enhance the heating effect of the gas in each of the gas circulation pipeline 220 and the gas extraction pipeline 230. The thermostatic water tank 310 may be provided with a second temperature sensor 311 and a liquidometer 312 for monitoring the temperature and liquid level, respectively, in the thermostatic water tank in real time.

Further, the sterilization gas supply assembly might further include, but is not limited to, a first gas filter, a first temperature sensor 130, a first check valve 140, a first valve 151, and a second valve. The first gas filter, the first temperature sensor 130, the first check valve 140, the first valve 151, and the second valve may each be disposed on the chemical feeding pipeline 110. The first gas filter and the first temperature sensor 130 may be both located between the thermostatic water tank 310 and the chemical feeding opening, while the first check valve 140 may be located between the thermostatic water tank 310 and the first temperature sensor 130, and the first valve 151 may be located at a side of the first check valve 140, adjacent to the first temperature sensor 130. The gas filter is advantageous for filtering impurities in the chemical feeding pipeline 110, improving the purity of the sterilization gas supplied to the container 20 and enhancing the sterilization effect. The first check valve 140 can prevent the sterilization gas from flowing backwards, thereby improving the safety factor of the whole container sterilization device 10. The provision of the first valve 151 and the second valve facilitates the maintenance and replacement of related pipelines and components.

Further, the gas circulation assembly further includes a pressure sensor 240, a first temperature and humidity sensor 251, a second temperature and humidity sensor 252, a third valve 261, a thirteenth valve 262, a ventilation branch pipeline 270, and an air filter 280.

The pressure sensor 240 may be disposed on the gas circulation pipeline 220 and located between the gas charging opening and the thermostatic water tank 310. The first temperature and humidity sensor 251, the second temperature and humidity sensor 252, and the third valve 261 may each be disposed on the gas extraction pipeline 230. The first temperature and humidity sensor 251 and the second temperature and humidity sensor 252 may be located between the vacuum pump 210 and the gas charging opening, spaced apart from each other. The third valve 261 may be located between the vacuum pump 210 and the thermostatic water tank 310. The gas circulation assembly might circulate the sterilization gas in the container 20 under the control of the control assembly, thereby enhancing the sterilization effect. In addition, the pressure in the gas circulation pipeline 220 and the temperature and humidity in the gas extraction pipeline 230 may be monitored in real time by the pressure sensor 240, the first temperature and humidity sensor 251, and the second temperature and humidity sensor 252, so that the gas circulation process can be better controlled according to the obtained monitoring data. The third valve 261 may facilitate the control of the communication between the vacuum pump 210 and the thermostatic water tank 310.

One end of the ventilation branch pipeline 270 may be in fluid communication with the gas circulation pipeline 220, and the other end of the ventilation branch pipeline 270 may be in fluid communication with outside air (i.e., the air in the environment exterior to the container sterilization device 10, or the like). The thirteenth valve 262 and the air filter 280 may be located on the ventilation branch pipeline 270. The arrangement may be such that the thirteenth valve 262 is closed during the gas circulation, and after the sterilization is completed and when the sterilization waste gas in the container 20 is pumped out for harmless gas treatment through the gas extraction pipeline 230, the container 20 may be in a negative pressure state. At this time, the thirteenth valve 262 may be opened, allowing outside air to be filtered by the air filter 280 and to enter the container 20.

In some embodiments, the heating and humidification assembly might further include, without limitation, a fourth valve 351 and a fifth valve 352. The fourth valve 351 may be disposed on the humidity feeding pipeline 340 and may be located between the steam generator 320 and the humidity feeding opening. The fifth valve 352 may be disposed between the thermostatic water tank 310 and the steam generator 320. The fourth valve 351 facilitates the control of the fluid communication between the steam generator 320 and the humidity feeding opening, while the fifth valve 352 facilitates the control of the fluid communication between the thermostatic water tank 310 and the steam generator 320.

According to some embodiments, the sterilization waste gas treatment assembly might include, but is not limited to, an exhaust pipeline 410, a second connecting pipeline 420, a third connecting pipeline 430, a fourth connecting pipeline 440, a fan 450, a sterilization waste gas treater 460, a sterilization substrate circulation changer, a tenth valve 471, an eleventh valve 472, a second check valve 481, and a third check valve 482. The sterilization waste gas treatment assembly can perform harmless gas treatment on the sterilization waste gas in the container 20, for example, by absorbing residual sterilization components in the sterilization waste gas, so that the sterilization waste gas reaches or satisfies safe emissions standards, and thus the environment is prevented from being polluted or contaminated.

Specially, the second connecting pipeline 420 may be used to provide fluid communication between the fan 450 and the vacuum pump 210. The third connecting pipeline 430 may be used to provide fluid communication between the fan 450 and the sterilization waste gas treater 460. The fourth connecting pipeline 440 may be used to provide fluid communication between the sterilization waste gas treater 460 and the sterilization substrate circulation changer. The exhaust pipeline 410 may be used to provide fluid communication between the sterilization waste gas treater 460 and the outside environment (i.e., the environment external to the container sterilization device 10, or the like). The fan 450 might introduce the air extracted by the vacuum pump 210 into the sterilization waste gas treater 460 through the third connecting pipeline 430 for harmless gas treatment, and, when the air reaches or satisfies the safe emissions standards, the air may be discharged through the exhaust pipeline 410. The sterilization substrate circulation changer can feed fresh sterilization substrate into the sterilization waste gas treater 460, thereby ensuring the continuous treating capacity of the sterilization waste gas treater 460. The tenth valve 471 may be disposed on the second connecting pipeline 420, while the eleventh valve 472 and the second check valve 481 may both be disposed on the third connecting pipeline 430, and the third check valve 482 may be disposed on the exhaust pipeline 410. The tenth valve 471 may be used to control the fluid communication between the vacuum pump 210 and the fan 450, while the eleventh valve 472 may be used to control the fluid communication between the fan 450 and the sterilization waste gas treater 460. The sterilization waste gas treater 460 may be provided with a check valve on either side thereof, which can effectively prevent gas reflux and can improve the safety factor.

According to some embodiments, the sterilization substrate circulation changer may include, without limitation, a sterilization substrate storage tank 491, a waste liquid recovery tank 492, a waste liquid recovery pipeline 493, a sterilization substrate liquid feeding pipeline 494, a circulation pump 495, a sixth valve 496a, a seventh valve 496b, an eighth valve 496c, and a ninth valve 496d.

In an embodiment, the waste liquid recovery pipeline 493 may be used to provide fluid communication between the waste liquid recovery tank 492 and the fourth connecting pipeline 440, while the sterilization substrate liquid feeding pipeline 494 may be used to provide fluid communication between the sterilization substrate storage tank 491 and the fourth connecting pipeline 440. The deactivated sterilization substrate in the sterilization waste gas treater 460 may be collected in the waste liquid recovery tank 492 through the fourth connecting pipeline 440 and the waste liquid recovery pipeline 493, while the sterilization substrate storage tank 491 might provide fresh sterilization substrate to the sterilization waste gas treater 460 through the sterilization substrate liquid feeding pipeline 494 and the fourth connecting pipeline 440, thereby ensuring ongoing or continual activity of the sterilization substrate in the sterilization waste gas treater 460.

In an embodiment, the circulation pump 495 may be disposed on the waste liquid recovery pipeline 493. Merely by way of example, in some cases, the circulation pump 495 may include, but is not limited to, a gear oil pump, or the like. The gear oil pump can circulate the sterilization substrate, can improve the efficiency of the sterilization substrate for treating the sterilization gas, and can additionally replace the sterilization substrate waste liquid, by feeding the fresh sterilization substrate into the sterilization waste gas treater 460 through the sterilization substrate liquid feeding pipeline 494 and the fourth connecting pipeline 440.

In an embodiment, the sixth valve 496a may be disposed on the waste liquid recovery pipeline 493 and may be located between the waste liquid recovery tank 492 and the circulation pump 495. The seventh valve 496b may be located at a junction of the waste liquid recovery pipeline 493, the sterilization substrate liquid feeding pipeline 494, and the fourth connecting pipeline 440. The eighth valve 496c may be located on the fourth connecting pipeline 440, and the ninth valve 496d may be located on the sterilization substrate liquid feeding pipeline 494. The sixth valve 496a may be used to control the fluid communication along the waste liquid recovery pipeline 493. The ninth valve 496d may be used to control the fluid communication along the sterilization substrate liquid feeding pipeline 494. The eighth valve 496c may be used to control the fluid communication along the fourth connecting pipeline 440, and the seventh valve 496b may be used to control the fluid communication between the sterilization waste gas treater 460 and the waste liquid recovery tank 492, and to control the fluid communication between the sterilization waste gas treater 460 and the sterilization substrate storage tank 491.

According to some embodiments, the cooling assembly may be used to cool the sterilization waste gas treater 460 and the vacuum pump 210. The cooling assembly might include, without limitation, a water feeding pipeline 510, a first water inlet pipeline 520, a first water outlet pipeline 530, a water filter 540, a twelfth valve 551, and a sixteenth valve 552.

In an embodiment, the sterilization waste gas treater 460 might have a first cooling water interlayer provided with a first cooling water interlayer inlet and a first cooling water interlayer outlet. The water feeding pipeline 510 may be provided with a water feeding opening 511 configured to be in fluid communication with a water source. In some cases, the water source may include, but is not limited to, a tap water source, or the like. The first water inlet pipeline 520 may be used to provide fluid communication between the first cooling water interlayer inlet and the water feeding pipeline 510, and the first water outlet pipeline 530 may be used to be in fluid communication with the first cooling water interlayer outlet to discharge the cooling water from the first cooling water interlayer. By flowing cooling water into and out of the first cooling water interlayer, the sterilization waste gas treater 460 can be cooled, thereby improving the treatment effect of the sterilization substrate on the sterilization gas. The water filter 540 may be disposed on the water feeding pipeline 510 and may be located between the water feeding opening 511 and a joint of the first water inlet pipeline 520 and the water feeding pipeline 510. The twelfth valve 551 may be disposed on the first water inlet pipeline 520. The water filter 540 can be used to filter impurities in the water (e.g., tap water, or the like). By opening and closing the twelfth valve 551, the water filtered by the water filter 540 through the water inlet can be controlled to cool the sterilization waste gas treater 460.

In an embodiment, the vacuum pump 210 might have a second cooling water interlayer provided with a second cooling water interlayer inlet and a second cooling water interlayer outlet. The second water inlet pipeline 560 may be used to provide fluid communication between the second cooling water interlayer inlet and the water feeding pipeline 510, and the second water outlet pipeline 570 may be used to provide fluid communication with the second cooling water interlayer outlet to discharge the cooling water from the second cooling water interlayer. By flowing cooling water into and out of the second cooling water interlayer, the vacuum pump 210 can be cooled, to prevent the vacuum pump 210 from being overheated, and the service life of the vacuum pump 210 may be prolonged. The fourteenth valve 353 may be disposed on the second water inlet pipeline 560. By opening and closing the fourteenth valve 353, the water filtered by the water filter 540, after passing through the water inlet, can be controlled to cool the vacuum pump 210.

In an embodiment, a discharge pipeline 580 may be further included. The first water outlet pipeline 530 and the second water outlet pipeline 570 may be in fluid communication with the discharge pipe 580. The discharge pipeline 580 may be used to discharge the water in the first water outlet pipeline 530 and the second water outlet pipeline 570 outward (i.e., to the exterior of the container sterilization device 10, or the like).

According to an embodiment, the mobile vehicle-mounted assembly 600 may be used to connect to the container 20. In an embodiment, the mobile vehicle-mounted assembly 600 may include, without limitation, one of a truck transportation assembly, or the mobile vehicle-mounted assembly 600 that includes a mobile carriage and a semi-trailer tractor, where the mobile carriage may be fixed on the semi-trailer tractor. The mobile carriage may be provided with a back door and a side door. The truck transportation assembly may be divided into large, medium, and small trucks with different specifications. The semi-trailer tractor and the mobile carriage can be fixed and separated, and after the semi-trailer tractor can transport the mobile carriage to a destination, the semi-trailer tractor can be separated from the mobile carriage to transport other standby mobile carriages again, so that one semi-trailer tractor can transport a plurality of mobile carriages. The carriage may be provided with a back door and a side door, so that the system can be conveniently checked and maintained.

In some embodiments, the parking support assembly 700 may be mounted below the mobile vehicle-mounted assembly 600 and may be used to support the mobile vehicle-mounted assembly 600.

According to some embodiments, the pipeline fixing support assembly might include, but is not limited to, a pipeline fixing rack 810, a pipeline fixing support arm 820, and a fixing rack support 830. The gas circulation pipeline 220, the gas extraction pipeline 230, the chemical feeding pipeline 110, and the humidity feeding pipeline 340 may each be fixed on the pipeline fixing rack 810. An end of the gas circulation pipeline 220 provided with the gas charging opening, an end of the gas extraction pipeline 230 provided with the gas extraction opening, an end of the chemical feeding pipeline 110 provided with the chemical feeding opening, and an end of the humidity feeding pipeline 340 provided with the humidity feeding opening can pass through the pipeline fixing rack 810 and can extend inside the container 20. The fixing rack support 830 may be fixed on one side of the mobile vehicle-mounted assembly 600. Each of the two ends of the pipeline fixing support arm 820 may respectively be fixed on one or the other of the pipeline fixing rack 810 and the fixing rack support 830. The fixing rack support 830 may be used to control the pipeline fixing support arm 820 to move the pipeline fixing rack 810.

Figure 4:
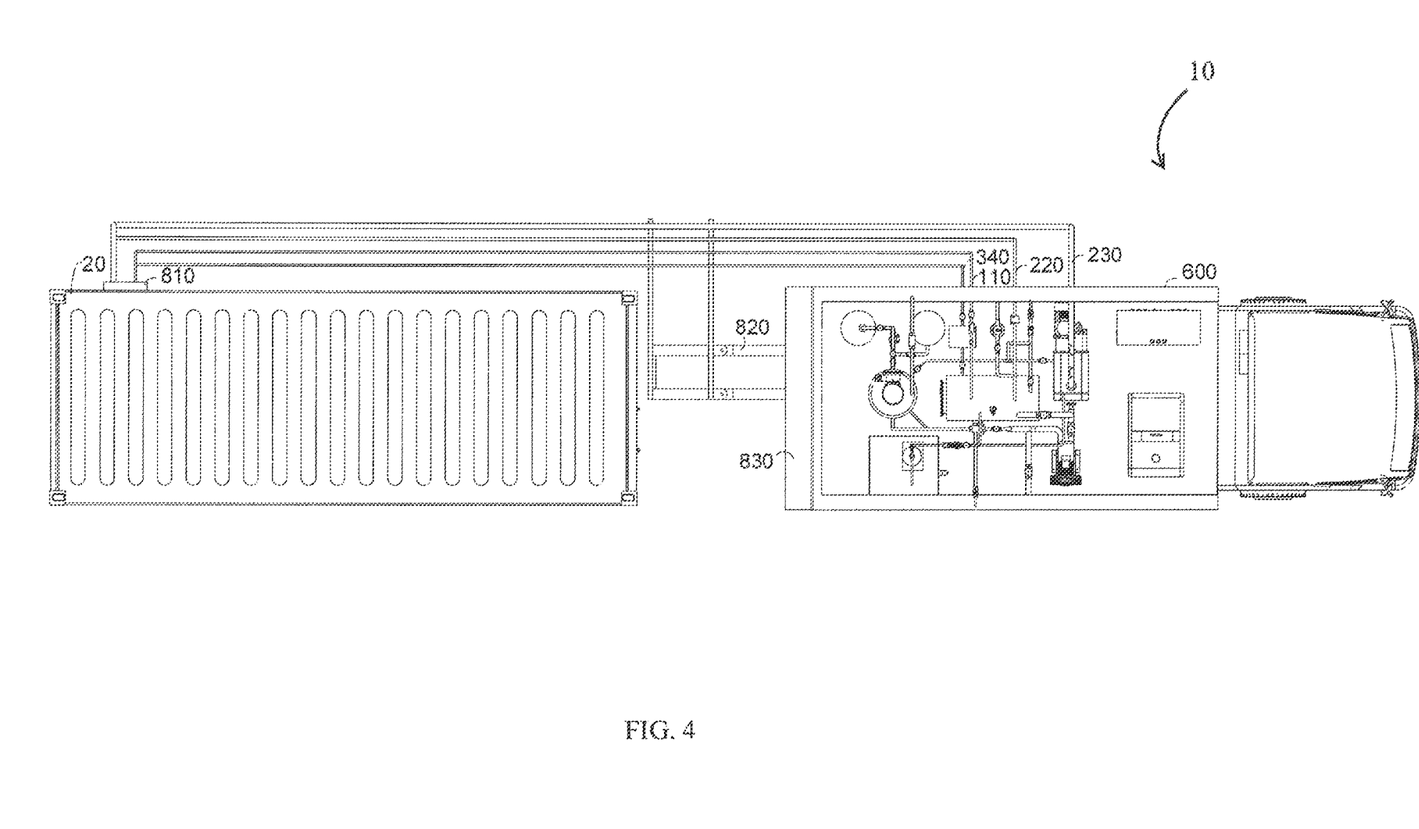
FIG. 4 is a top view of a container sterilization system according to another embodiment of the present disclosure.

In this embodiment, as shown in FIG. 2, the pipeline fixing rack 810 may be fixed to the front of the container 20. Of course, in other embodiments, as shown in FIG. 4, the pipeline fixing rack 810 may also be fixed to a side of the container 20. Although not shown, in yet other embodiments, the pipeline fixing rack 810 may be fixed to a top portion or a rear portion of the container 20.

The control assembly might include, without limitation, a controller 910, a power supply 920, a control interface 930, and a control cabinet. The controller 910 may be a programmable controller 910 for controlling the opening and closing of each valve, for controlling operations of each of the vacuum pump 210, the thermostatic water tank 310, the steam generator 320, the fan 450, and the circulation pump 495, and for processing data obtained from each of the first temperature sensor 130, the second temperature sensor 311, the first temperature and humidity sensor 251, the second temperature and humidity sensor 252, and the pressure sensor 240, so as to achieve automatic control. The power supply 920 may include, but is not limited to, a diesel generator, or the like, while the control interface 930 may include, without limitation, an operable touch screen, or the like.

The vacuum pump 210, the thermostatic water tank 310, and the steam generator 320 may each be electrically coupled to the controller 910, and the controller 910 may be used to control corresponding operations of each of the vacuum pump 210, the thermostatic water tank 310, and the steam generator 320.

The operational processes of the aforementioned container sterilization device 10 and the container sterilization system may be as follows:

1) The power supply 920, the controller 910, and the control interface 930 may be switched on to control the pipeline fixing support arm 820 to connect the pipeline fixing rack 810 and the container 20 together.

2) The tap water pipeline may be in fluid communication with the water feeding opening 511, and the fourteenth valve 353 may be opened. The tap water may be filtered by the water filter 540 and may be injected into the thermostatic water tank 310. The liquid level may be monitored by the liquidometer 312 until a set water level is reached, at which point the water injection may be stopped.

3) The thermostatic water tank 310 may be heated to a temperature within a range from 60° C. to 80° C., during which the first temperature sensor 130 may be used to detect the water temperature, so as to provide hot water for the heating and humidification assembly and to supply heat to each of the sterilization gas supply assembly and the gas circulation assembly.

4) The vacuum pump 210 and the fan 450 may be switched on, while the tenth valve 471 and the fifteenth valve 496e may be opened, and the other valves may be closed, then the container 20 may be vacuumized to a pressure within a range from −30 kPa to −70 kPa.

5) The fourth valve 351, the steam generator 320, and the fifth valve 352 may be turned on or opened, as appropriate, while the other valves may be closed, and the water in the thermostatic water tank 310 may be injected into the container 20 through the humidity feeding pipeline 340 via the steam generator 320 to humidify the container 20.

6) The first valve 151 and second valve may be opened, while other valves may be closed. The sterilization gas may be filtered by the first gas filter, then may be heated and vaporized by the thermostatic water tank 310, and then may be injected into the container 20 through the chemical feeding pipeline 110 until the pressure reaches between 20 kPa and 50 kPa. The temperature of sterilization gas may be detected by first temperature sensor 130.

7) In the sterilization circulation, the third valve 261 may be opened and the vacuum pump 210 may be switched on, and other valves may be closed. The sterilization gas in the container 20 may be extracted out through the gas extraction pipeline 230 by the vacuum pump 210, then may be heated by the thermostatic water tank 310, and then may again enter the container 20 through the gas circulation pipeline 220. The sterilization gas in the container 20 may be circulated and heated in this way and the container 20 may be continuously humidified by the process at Step (5) to maintain the temperature inside the container 20 at between 40° C. and 50° C. and to maintain the humidity inside the container 20 at between 50% RH and 70% RH. The sterilization process may be performed for 6 h to 8 h under these conditions. The temperature and humidity may be detected by the first temperature and humidity sensor 251 and the second temperature and humidity sensor 252, and the pressure may be detected by the pressure sensor 240. At the same time, the sixteenth valve 552 may be opened again, and the tap water may be introduced through the water feeding opening 511, may be filtered by the water filter 540, then may enter the second cooling water interlayer to cool the vacuum pump 210, and then may be discharged outside the container sterilization device 10 by the second water outlet pipeline 570 and the discharge pipeline 580.

8) In the treatment and replacement of waste gas, after the sterilization has been completed, the sterilization waste gas in the container 20 may be treated by the sterilization waste gas treatment assembly, so that the waste gas emission meets safety emissions requirements. In addition, the fresh air filtered by the air filter 280 may enter the container 20 to replace the residual sterilization gas, and the replaced sterilization waste gas may then be subjected to harmless gas treatment. The specific operational steps for harmless gas treatment may be as follows:

(a) The seventh valve 496b, the ninth valve 496d, and the circulation pump 495 may be switched on or opened, as appropriate, and the fresh sterilization substrate in the sterilization substrate storage tank 491 may be pumped into the sterilization waste gas treater 460 through the sterilization substrate liquid feeding pipeline 494 by using the circulation pump 495. After a certain amount of pumping, the seventh valve 496b, the ninth valve 496d, and the circulation pump 495 may be switched off or closed, as appropriate, to complete the pumping of the fresh sterilization substrate.

(b) After the sterilization has been completed, all the devices may be switched off or closed, as appropriate, and the seventh valve 496b, the eighth valve 496c, the eleventh valve 472, the twelfth valve 551, and the tenth valve 471 may be opened, then the fan 450, the vacuum pump 210, and the circulation pump 495 may be switched on, and the sterilization waste gas in the container 20 may be extracted into the sterilization waste gas treater 460 by using the vacuum pump 210 for treatment. The sterilization substrate in the sterilization waste gas treater 460 may be circulated and uniformly mixed by using the circulating pump 495, and the second check valve 481 prevents the sterilization waste gas from flowing backwards. The cooling water enters the first cooling water interlayer of the sterilization waste gas treater 460 from the first cooling water interlayer inlet to cool the sterilization waste gas treater 460 down, and then may be discharged from the first cooling water interlayer outlet. The residual waste gas after the harmless gas treatment may be discharged from the exhaust opening at the top of the sterilization waste gas treater 460 through the exhaust pipeline 410, and the third check valve 482 prevents the residual sterilization waste gas after the harmless gas treatment from flowing backwards.

(c) When the pressure in the container 20 reaches between −50 kPa and −80 kPa, the seventh valve 496b, the eighth valve 496c, the eleventh valve 472, the twelfth valve 551, and the tenth valve 471 may be closed, while the fan 450, the vacuum pump 210, and the circulation pump 495 may be switched off, and the gas that is extracted to the sterilization waste gas treater 460 may be stopped. The thirteenth valve 262 may be opened, and the air that is external to the container sterilization device 10 may be injected into the container 20, using the pressure difference, via gas circulation pipeline 220 after filtering by the air filter 280, to replace the sterilization gas. When normal pressure (e.g., ambient pressure, or the like) has been reached, the thirteenth valve 262 may be closed.

(d) The Steps (b) and (c) may be repeated for a plurality of times.

(e) The pipeline fixing rack 810 may be removed from the container 20, and the pipeline fixing support arm 820 may be stored.

(f) Recycling the waste liquid in the sterilization waste gas treater 460 after a plurality of times of sterilization may be performed according to the following non-limiting example implementation: the sixth valve 496a and the eighth valve 496c may be opened, the circulating pump 495 may be switched on, and the waste liquid of the sterilization waste gas treater 460 may be pumped into the waste liquid recovery tank 492 through the waste liquid recovery pipeline 493 by using the circulation pump 495. The sixth valve 496a and the eighth valve 496c may then be closed, and the circulation pump 495 may be switched off, and the recovery of the waste liquid may be completed.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A container sterilization device, comprising:
   a sterilization gas supply assembly comprising a chemical feeding pipeline provided with a chemical feeding opening;
   a gas circulation assembly comprising a vacuum pump, a gas circulation pipeline provided with a gas charging opening, and a gas extraction pipeline provided with a gas extraction opening; and
   a heating and humidification assembly comprising a thermostatic water tank, a steam generator, a first connecting pipeline, and a humidity feeding pipeline, the humidity feeding pipeline being provided with a humidity feeding opening;
   wherein the chemical feeding pipeline is at least partially located in the thermostatic water tank;
   wherein an end of the gas circulation pipeline that is opposite from the gas charging opening is configured to be in fluid communication with an end of the gas extraction pipeline that is opposite from the gas extraction opening, wherein a joint connecting the gas circulation pipeline with the gas extraction pipeline and a portion of pipelines adjacent to the joint are located in the thermostatic water tank, and wherein the vacuum pump is disposed on the gas extraction pipeline between the gas extraction opening and the thermostatic water tank; and
   wherein the first connecting pipeline is configured to provide fluid communication between the thermostatic water tank and the steam generator, and wherein an end of the humidity feeding pipeline that is opposite from the humidity feeding opening is configured to be in fluid communication with the steam generator.

2. The container sterilization device according to claim 1, wherein at least one of the chemical feeding pipeline, the gas circulation pipeline, or the gas extraction pipeline is at least partially disposed in the thermostatic water tank in a spirally folded manner.

3. The container sterilization device according to claim 1, wherein the sterilization gas supply assembly further comprises a first gas filter, a first temperature sensor, a first check valve, a first valve, and a second valve; wherein the first gas filter, the first temperature sensor, the first check valve, the first valve, and the second valve are disposed on the chemical feeding pipeline; and wherein the first gas filter and the first temperature sensor are located between the thermostatic water tank and the chemical feeding opening, the first check valve is located between the thermostatic water tank and the first temperature sensor, and the first valve is located at a side of the first check valve adjacent to the first temperature sensor.

4. The container sterilization device according to claim 1, wherein the gas circulation assembly further comprises a pressure sensor, a first temperature and humidity sensor, a second temperature and humidity sensor, and a third valve; wherein the pressure sensor is disposed on the gas circulation pipeline and is located between the gas charging opening and the thermostatic water tank; wherein the first temperature and humidity sensor and the second temperature and humidity sensor are disposed on the gas circulation pipeline, the first temperature and humidity sensor and the second temperature and humidity sensor being located between the vacuum pump and the gas charging opening, spaced apart from each other; and wherein the third valve is disposed on the gas circulation pipeline and is located between the vacuum pump and the thermostatic water tank.

5. The container sterilization device according to claim 1, wherein the heating and humidification assembly further comprises a fourth valve and a fifth valve, the fourth valve being disposed on the humidity feeding pipeline and being located between the steam generator and the humidity feeding opening, and the fifth valve being disposed between the thermostatic water tank and the steam generator.

6. The container sterilization device according to claim 1, further comprising:
   a sterilization waste gas treatment assembly comprising a second connecting pipeline, a third connecting pipeline, a fourth connecting pipeline, a fan, a sterilization waste gas treater, a sterilization substrate circulation changer, and an exhaust pipeline;
   wherein the second connecting pipeline is configured to provide fluid communication between the vacuum pump and the fan, the third connecting pipeline is configured to provide fluid communication between the fan and the sterilization waste gas treater, the fourth connecting pipeline is configured to provide fluid communication between the sterilization waste gas treater and the sterilization substrate circulation changer, the exhaust pipeline is configured to provide fluid communication between the sterilization waste gas treater and an outside environment.

7. The container sterilization device according to claim 6, wherein the sterilization substrate circulation changer comprises a waste liquid recovery tank, a waste liquid recovery pipeline, a sterilization substrate storage tank, and a sterilization substrate liquid feeding pipeline; wherein the waste liquid recovery pipeline is configured to provide fluid communication between the waste liquid recovery tank and the fourth connecting pipeline, and the sterilization substrate liquid feeding pipeline is configured to provide fluid communication between the sterilization substrate storage tank and the fourth connecting pipeline.

8. The container sterilization device according to claim 7, wherein the sterilization substrate circulation changer further comprises a circulation pump disposed on the waste liquid recovery pipeline.

9. The container sterilization device according to claim 8, wherein the sterilization substrate circulation changer further comprises a sixth valve, a seventh valve, an eighth valve, and a ninth valve; wherein the sixth valve is disposed on the waste liquid recovery pipeline and is located between the waste liquid recovery tank and the circulation pump; wherein the seventh valve is disposed at a junction of the waste liquid recovery pipeline, the sterilization substrate liquid feeding pipeline, and the fourth connecting pipeline; wherein the eighth valve is disposed on the fourth connecting pipeline; and wherein the ninth valve is disposed on the sterilization substrate liquid feeding pipeline.

10. The container sterilization device according to claim 6, wherein the sterilization waste gas treatment assembly further comprises a tenth valve, an eleventh valve, a second check valve, and a third check valve; wherein the tenth valve is disposed on the second connecting pipeline, the eleventh valve is disposed on the third connecting pipeline, the second check valve is disposed on the third connecting pipeline, and the third check valve is disposed on the exhaust pipeline.

11. The container sterilization device according to claim 6, further comprising:
- a cooling assembly comprising a water feeding pipeline, a first water inlet pipeline, and a first water outlet pipeline;
- wherein the water feeding pipeline is provided with a water feeding opening configured to be in fluid communication with a water source;
- wherein the sterilization waste gas treater has a first cooling water interlayer provided with a first cooling water interlayer inlet and a first cooling water interlayer outlet, wherein the first water inlet pipeline is configured to provide fluid communication between the first cooling water interlayer inlet and the water feeding pipeline, and wherein the first water outlet pipeline is configured to be in fluid communication with the first cooling water interlayer outlet to discharge cooling water from the first cooling water interlayer.

12. The container sterilization device according to claim 11, wherein the cooling assembly further comprises a water filter and a twelfth valve; wherein the water filter is disposed on the water feeding pipeline and is located between the water feeding opening and a joint connecting the first water inlet pipeline and the water feeding pipeline; and wherein the twelfth valve is disposed on the first water inlet pipeline.

13. The container sterilization device according to claim 11, wherein the cooling assembly further comprises a second water inlet pipeline and a second water outlet pipeline; wherein the vacuum pump has a second cooling water interlayer provided with a second cooling water interlayer inlet and a second cooling water interlayer outlet; wherein the second water inlet pipeline is configured to provide fluid communication between the second cooling water interlayer inlet and the water feeding pipeline; and wherein the second water outlet pipeline is configured to be in fluid communication with the second cooling water interlayer outlet to discharge cooling water from the second cooling water interlayer.

14. The container sterilization device according to claim 13, wherein the cooling assembly further comprises a sixteenth valve disposed on the second water inlet pipeline.

15. The container sterilization device according to claim 1, further comprising:
- a mobile vehicle-mounted assembly connecting to a container;
- wherein the sterilization gas supply assembly, the gas circulation assembly, and the heating and humidification assembly are mounted on the mobile vehicle-mounted assembly.

16. The container sterilization device according to claim 15, wherein the mobile vehicle-mounted assembly comprises one of:
- a truck transportation assembly; or
- a mobile carriage and a semi-trailer tractor, wherein the mobile carriage is fixed on the semi-trailer tractor.

17. The container sterilization device according to claim 15, further comprising:
- a parking support assembly mounted below the mobile vehicle-mounted assembly and configured to support the mobile vehicle-mounted assembly.

18. The container sterilization device according to claim 15, further comprising:
- a pipeline fixing support assembly comprising a pipeline fixing rack, a pipeline fixing support arm, and a fixing rack support;
- wherein the gas circulation pipeline, the gas extraction pipeline, the chemical feeding pipeline, and the humidity feeding pipeline are fixed on the pipeline fixing rack;
- wherein an end of the gas circulation pipeline that is provided with the gas charging opening, an end of the gas extraction pipeline that is provided with the gas extraction opening, an end of the chemical feeding pipeline that is provided with the chemical feeding opening, and an end of the humidity feeding pipeline that is provided with the humidity feeding opening pass through the pipeline fixing rack;
- wherein the fixing rack support is fixed on one side of the mobile vehicle-mounted assembly, each of two ends of the pipeline fixing support arm being respectively fixed on one or the other of the pipeline fixing rack and the fixing rack support, and wherein the fixing rack support is configured to control the pipeline fixing support arm to move the pipeline fixing rack.

19. The container sterilization device according to claim 1, further comprising:
- a controller;
- wherein the vacuum pump, the thermostatic water tank, and the steam generator are electrically coupled to the controller, the controller controlling operations of the vacuum pump, the thermostatic water tank, and the steam generator.

20. A container sterilization system, comprising:
- a container; and
- a container sterilization device, comprising:
  - a sterilization gas supply assembly comprising a chemical feeding pipeline provided with a chemical feeding opening;
  - a gas circulation assembly comprising a vacuum pump, a gas circulation pipeline provided with a gas charging opening, and a gas extraction pipeline provided with a gas extraction opening; and
  - a heating and humidification assembly comprising a thermostatic water tank, a steam generator, a first connecting pipeline, and a humidity feeding pipeline, the humidity feeding pipeline being provided with a humidity feeding opening;
  - wherein the chemical feeding pipeline is at least partially located in the thermostatic water tank;
  - wherein an end of the gas circulation pipeline that is opposite from the gas charging opening is configured to be in fluid communication with an end of the gas extraction pipeline that is opposite from the gas extraction opening, wherein a joint connecting the gas circulation pipeline with the gas extraction pipeline and a portion of pipelines adjacent to the joint are located in the thermostatic water tank, and wherein the vacuum pump is disposed on the gas extraction pipeline between the gas extraction opening and the thermostatic water tank; and
  - wherein the first connecting pipeline is configured to provide fluid communication between the thermostatic water tank and the steam generator, and wherein an end of the humidity feeding pipeline that is opposite from the humidity feeding opening is configured to be in fluid communication with the steam generator;
  - wherein the chemical feeding opening, the gas charging opening, the gas extraction opening, and the humidity feeding opening are in fluid communication with an interior of the container.

* * * * *